United States Patent [19]

Maeda et al.

[11] Patent Number: 5,118,616
[45] Date of Patent: Jun. 2, 1992

[54] METHOD OF PRODUCING SUBSTANCES IN LIVING SILKWORMS

[75] Inventors: Susumu Maeda, Tottori; Mitsuru Furusawa, Tokyo, both of Japan

[73] Assignee: Daiichi Seiyaku Co., Ltd., Tokyo, Japan

[21] Appl. No.: 684,486

[22] Filed: Apr. 12, 1991

Related U.S. Application Data

[63] Continuation of Ser. No. 747,216, Jun. 21, 1985, abandoned.

[30] Foreign Application Priority Data

Jun. 21, 1984 [JP] Japan ................. 59-128215

[51] Int. Cl.$^5$ ............ C12P 21/00; C12N 15/00; C12N 1/21
[52] U.S. Cl. .................. 435/69.1; 435/320.1; 435/252.33; 435/235.1
[58] Field of Search ............ 435/320.1, 69.1, 235.1, 435/252.33

[56] References Cited

U.S. PATENT DOCUMENTS 4,745,051 5/1988 Smith et al. ............ 435/69.51

FOREIGN PATENT DOCUMENTS

A0127839 12/1984 European Pat. Off. .
A0155476 9/1985 European Pat. Off. .

OTHER PUBLICATIONS

Nature, vol. 315, News & Views, pp. 628–629, (1985).
New Scientist, vol. 11, p. 25 (1985).
Gene 58, pp. 273–281, Miyajima et al (1987).
Proc. Natl. Acad. Sci USA vol. 87, pp. 2760–2764, Medin et al (1990).
DNA, vol. 7, pp. 417–422, Price et al (1988).
Eur J Biochem, 187, pp. 699–703 (1990) Gunne et al.
Proc. Natl. Acad. Sci USA, vol. 86, pp. 1453–1456, Price et al, (1989).
Maeda et al. (1984) Proc. Japan Acad. 60: 423–6.
Maeda et al. (1985) Nature 315: 592–4.
Iatrou et al. (1985) J. Virology 54: 436–4.
Miller (1982) in *Genet. Eng. in Eukaryotes*, ed. Lurquin et al. pp. 89–97.
Rohrmann et al. (1981) J. Molecular Evolution 17: 329–33.
Pennock et al. (1984) Molecular and Cellular Biology 4: 399–406.
Smith et al. (1983) Molecular and Cellular Biology 3: 2156–65.
R. E. F. Matthews: "Classification and Nomenclature of Viruses", Third Report to the International Committee on Taxonomy of Viruses, 1979, pp. 170, 171, S. Karger, Basel, CH.

*Primary Examiner*—Richard A. Schwartz
*Assistant Examiner*—S. L. Nolan
*Attorney, Agent, or Firm*—Sughrue, Mion, Zinn, Macpeak & Seas

[57] ABSTRACT

A method of producing useful substances which comprising propagating in cultured cells or in a host a recombinant *Bombyx mori* nuclear polydegrosis virus (BmNPV) DNA is disclosed. The BmNPV DNA is produced by recombination with a double-stranded DNA containing (i) a 5'-upstream BmNPV DNA fragment orginally occurring upstream from the structural gene coding for the production of polyhedral protein and also including the promoter region for the structural gene, (ii) a translational start codon and (iii) a gene coding for the production of a useful substance exogenous to the virus, with or without (iv) a 3'-downstream BmNPV DNA fragment originally occurring downstream from the structural gene coding for the production of polyhedral protein.

8 Claims, 10 Drawing Sheets

```
                          -382
                                    CAGGAAGAGGTTTATACTAAAC
              5'
TGTTACATTGCAAACGTGGTTTCGTGTACCAAATGTGAAA
ACCGATGTTTGATCAAGGCTCTGACACATTTTTACAATTA
CGACTCCAAGTGTGTGGGTGAAGTCATGCATCTTTTAATC
AAATCCAAGATGTGTATAAACCACCAAACTGCCAAAAAA
TGAAAACTGTCGACAAGCTCTGTCCGTTTGCTGGCAACTG
CAAGGGCCTCAATCCTATTTGTAATTATTGAACAATAAAA
CAATTATAAATGTCAAATTTGTTTTTTATTAACGATACAA
ATGGAAATAATAACCATCTCGCAAATAAATAAGTATTTTA
CTGTTTTCGTAACAGTTTTGTAATAAAAAACCTATAAAT
123
ATGCCGAATTATTCATACACCCCCACCATCGGGCGTACTT
ACGTGTACGACAATAAATATTACAAAAACTTGGGCTGTCT
TATCAAAAACGCCAAGCGCAAGAAGCACCTAGTCGAACAT
GAACAAGAGGAGAAGCAATGGGATCTTCTAGACAACTACA
TGGTTGCGCAAGATCCCTTTTTAGGACCGGGCAAAAACCA
AAAACTTACCCTTTTTAAAGAAATTCGCAGTGTGAAACCC
GATACCATGAAGTTAATCGTCAACTGGAGCGGCAAAGAGT
TTTTGCGTGAAACTTGGACCCGTTTTGTTGAGGACAGCTT
CCCCATTGTAAACGACCAAGAGGTGATGGACGTGTACCTC
GTCGCCAACCTCAAACCCACACGCCCCAACAGGTGCTACA
AGTTCCTCGCTCAACACGCTCTTAGGTGGAAGAAGACTA
CGTGCCCCACGAAGTAATCAGAATTATGGAGCCATCCTAC
GTGGGCATGAACAACGAATACAGAATTAGTCTGGCTAAAA
AGGGCGGCGGCTGCCCAATCATGAACATCCACAGCGAGTA
```

Fig. 3B.

```
CACCAACTCGTTCGAGTCGTTTGTGAACCGCGTCATATGG
GAGAACTTCTACAAACCCATCGTTTACATCGGCACAGACT
CTGCCGAAGAAGAGGAAATCCTAATTGAGGTTTCTCTCGT
TTTCAAAATAAAGGAGTTTGCACCAGACGCGCCTCTGTTC
ACTGGTCCGGCGTATTAAACACTATACATTGTTATTAGT
ACATTTATTAAGCGTTAGATTCTGTGCGTTGTTGATTTAC
AGACAATTGTTGTACGTATTTAATAATTCATTAAATTTG
TAATCTTTAGGGTGGTATGTTAGAGCGAAAATCAAATGAT
TTTCACGTAGTCTTTGTATCTGAATTTAAATATTAAATCC
TCAATAGATTTGTAAAATAGGTTTCGATTGGTTTCAAACA
AGGGTTGTTTTTGCAAACCGATGGCTGGACTATCTAATGG
ATTTTCGCTCAACACCACACGACTTGCCAAATCTTGTAGC
AGCAATCTAGCTTTGTCGATATTCGTTTGTGTTTTGTTTT
GTAATAAAGATTCGACGTCGTTCAAAATATTATGCGCTTT
TGTATTTTTTTCATCACTGTCGTTGGTGTACAATTGACTC
GACGTAAACACGTTAAATAAAGCTT                3'
                                       1185
```

585→|
                      -1   1 2 3   4 5 6   7 8 9  10 11 12
    A A C C|T A T A A A T - A T G - C C G - A A T - T A T -
                               Pro     Asn     Tyr
                               312→|
    131415  161718  192021  222324  252627  282930  313233
    T C A - T A C - A C C - C C C - A C C - A T C - G       - 3'
     Ser     Tyr
```

METHOD OF PRODUCING SUBSTANCES IN LIVING SILKWORMS

This is a continuation of application Ser. No. 06/747,216 filed Jun. 21, 1985, now abandoned.

BACKGROUND OF THE INVENTION

1. Field of the Invention

This invention relates to a method of producing substances useful, for instance, as drugs by utilizing genetic engineering techniques, in particular to a method of producing such substances more efficiently as compared with conventional methods. More specifically, this invention relates to a method of producing such substances in vitro or in vivo by making use of a viral DNA. In a further aspect, this invention relates to a method of producing various useful substances efficiently in vivo in silkworms (*Bombyx mori*) by making use of a nuclear polyhedrosis virus. The invention also relates to vectors and recombinant viral DNAs, which are useful in carrying out the above-mentioned methods, as well as a method of producing the same.

2. Description of the Prior Art

A number of methods have been reported of producing useful substances in *Escherichia coli, Bacillus subtilis, Saccharomyces cereviciae,* and so forth by using plasmids and the like and taking advantage of recombinant DNA techniques.

There is also a report describing an attempt to produce β-interferon and β-galactosidase in cultured cells (of an established cell line from *Spodoptera frugiperda*) by using viral DNA (*Autographa californica* nuclear polyhedrosis virus DNA) after structural gene substitution therein G. E. Smith et al., *Molecular and Cellular Biology*, 3 (12), 2156–2165 (1983); G. D. Pennock et al., ibid., 4 (3), 399–406 (1984). However, it is a problem that *A. californica* which is to be used in carrying out this method is a pest existing in nature. Therefore, this method is not satisfactory as a method of producing useful substances. The present inventors conducted investigations in an attempt to provide a more improved method of producing useful substances and have now completed the present invention.

SUMMARY OF THE INVENTION

This invention thus provides a method of producing useful substances, such as proteins or glycoproteins, by genetic engineering utilizing the DNA of *Bombyx mori* nuclear polyhedrosis virus (hereinafter abbreviated as BmNPV). More particularly, this invention provides a method of producing useful substances efficiently by taking advantage of the function of a promoter region in the BmNPV DNA; recombinant DNAs derived from BmNPV DNA by recombination with exogenous genes coding for the production of useful substances; and recombination vectors useful for such recombination.

The invention also provides a method of transfection using in combination with BmNPV a recombinant transfer vector which contains a 5'-upstream BmNPV DNA fragment originally occurring upstream from the structural gene for polyhedral protein and still including the promoter region for the structural gene, a translational start codon and an exogenous gene coding for the production of a useful substance (i.e., a gene foreign thereto), with or without a 3'-downstream BmNPV DNA fragment originally occurring downstream from the structural gene for polyhedral protein.

The invention further provides a method of producing useful substances which comprises either forming a recombinant BmNPV by inoculating culture cells or a living silkworm with a mixture of a recombinant transfer vector and BmNPV DNA to thereby form the recombinant BmNPV in the cells or living organism, or inoculating cultured cells or living silkworms in the same manner with a recombinant BmNPV constructed by preparing a joined DNA from BmNPV DNA and an *Escherichia coli* plasmid such as pBR322 and further substituting a gene for the production of a useful substance for the structural gene for polyhedral protein as contained in the recombinant DNA or by some other appropriate method, and propagating the recombinant BmNPV in the cells or living organism.

In a particular aspect, the invention provides a method of producing useful substances which comprises propagating in cultured cells or in a host (in particular an established cell line from *Bombyx mori* or in living silkworms) a recombinant *Bombyx mori* nuclear polyhedrosis virus (BmNPV) produced by recombination with a double-stranded DNA containing a 5'-upstream BmNPV DNA fragment originally occurring upstream from the structural gene for polyhedral protein and still including the promoter region for the structural gene, a translational start codon and a gene coding for the production of a useful substance, with or without a 3'-downstream BmNPV DNA fragment originally occurring downstream from the structural gene for polyhedral protein.

In another aspect, the invention provides a vector which contains a 5'-upstream BmNPV DNA fragment originally occurring upstream from the structural gene for polyhedral protein and still including the promoter for said structural gene and a 3'-downstream BmNPV DNA fragment originally occurring downstream from the structural gene and, further, the vector as just mentioned in which the 5'-upstream DNA fragment is followed by a translational start codon and a gene coding for the production of a useful substance.

In a further aspect, the invention provides a method of producing useful substances which comprises excising from the BmNPV DNA the structural gene for polyhedral protein together with a 5'-upstream portion upstream from the structural gene and including the promoter region for the structural gene and a 3'-downstream portion downstream from the structural gene, substituting a gene coding for the production of a useful substance for the structural gene portion of the DNA fragment obtained, inserting the substitution product into a vector, introducing the thus-produced recombinant DNA for transfer combined with the BmNPV DNA into cells or a living host for transfection, and propagating the resultant recombinant BmNPV DNA; a recombinant BmNPV DNA produced by recombination with a gene coding for the production of a useful substance such as a heterologous gene; the recombinant BmNPV DNA as just mentioned in which the recombination comprises substitution in the polyhedral protein gene region and/or insertion in some other region than that occupied by the polyhedral protein gene; a method of producing useful substances by genetic engineering which comprises utilizing BmNPV DNA as a vector; and a method of producing useful substances by genetic engineering which comprises utilizing a 5'-upstream BmNPV DNA portion originally occurring upstream from the structural gene for polyhedral protein and still including the promoter region for the structural gene and a 3'-downstream BmNPV DNA portion originally occurring downstream from the structural gene.

DETAILED DESCRIPTION OF THE INVENTION

The invention will become more apparent through the description of typical modes of practice of the invention which follows.

BmNPV is one of the insect viruses belonging to the baculovirus group. It has high host specificity and infects the silkworm (*Bombyx mori*) with accumulation of polyhedral protein in large amounts in the cells thereof. This virus has a double-stranded, circular DNA genome of about 140 kbp and this DNA can be obtained from viral particles using conventional techniques, for example by protease treatment, sodium lauryl sulfate (SDS) treatment, etc. and extraction, etc., as described in G. E. Smith and M. D. Summers, *Virology*, 89, 517-527 (1978). This double-stranded circular DNA (hereinafter referred to briefly as viral DNA or BmNPV DNA) is a fairly large circular DNA. It is therefore preferable to select for use a smaller DNA fragment containing the structural gene for polyhedral protein and portions before and behind the gene (5'-upstream and 3'-downstream portions) from among DNA fragments produced by restriction enzyme treatment. Various restriction enzymes are known and are available on the market. Therefore the selection of an appropriate one or ones for the above purpose is easy and appropriate conditions of use thereof can be selected depending on the enzyme or enzymes employed as described in T. Maniatis, E. F. Fritsch, J. Sambrook, *Molecular Cloning* (hereinafter, Mol. Clon.), Cold Spring Harbor Laboratory, 1982, pp 97-148. The Synthesis (chemical synthesis, cleavage with restriction enzyme or enzymes), separation and detection of DNA fragments, analysis of DNA sequences and treatment of *Escherichia coli* etc.(transformation, cultivation, plasmid recovery, etc.), involved in the technological contents of the present invention can be performed using well known genetic engineering techniques as described in A. D. Riggs and K. Itakura, *Am. J. Hum. Genet.*, 31, 531-538 (1979) and *Mol. Clon.*

In selecting a DNA fragment containing a structural gene portion from among a number of DNA fragments produced from BmNPV DNA, Southern hybridization (Mol. Coln., pp 382-389) using a probe prepared in a conventional manner is helpful among others. While the fragment to be selected must contain the structural gene portion, what is important is that the fragment also contains a fairly long DNA chain on the 5' side (upstream side) and, in some instances, such a DNA chain also on the 3' side (downstream side). The length of each chain is of importance in connection with the efficiency of production of the desired useful substance. Although ease of handling is also a factor of significance, as will be mentioned hereinafter, whether a given chain length is adequate or not can be ascertained experimentally. The adequate chain length of DNA was determined as follows. With DNA fragments of different length, recombinant viruses containing a gene for the production of a useful substance such as α-IFN were constructed as described in Example 1. Then, culture cells were infected with these recombinant viruses to compare the productivity of the useful substance. When guided by the description which follows, in particular the examples, one of ordinary skill in the art would not encounter any serious difficulties in carrying out experiments necessary in this connection even if some time and labor are required. Whereas a fragment of about 10.6 kbp obtainable by cleavage with EcoRI (produced by Takara Shuzo Co., Ltd.) is one of the fragments suited for the purpose, a variety of fragments, e.g., ClaI-ClaI, PstI-PstI, etc. obtainable by using other restriction enzymes may also be usable. ClaI is produced by New England Biolabs, USA, and PstI is produced by Takara Shuzo Co., Ltd.

Efficient use can be made of various techniques in eliminating the structural gene portion from a fragment containing the structural gene for polyhedral protein with the preceding and succeeding DNA chains and removing for use a DNA chain having an appropriate length and containing the promoter region on the side upstream from the structural gene and, as the case may be, a DNA chain having an appropriate length and originally occurring downstream from the structural gene.

Thus, fragments obtained by using various restriction enzymes are examined for their DNA sequences to thereby identify the structural gene portion so that the structural gene can be eliminated by digestion using exonuclease enzymes (e.g., by digestion with Bal31 or exonuclease III). The upstream and downstream DNA chain which are required may be prepared, for example, as portions remaining after Bal31 digestion, or by restriction enzyme cleavage following determination of the respective DNA sequences, or by chemical synthesis as described in A. D. Riggs and K. Itakura, *Am. J. Hum. Genet.*, 31, 531-538 (1979).

The amino acid sequence of the polyhedral protein of BmNPV produced in the silkworm has been analyzed and reported to include 244 amino acids by *Invertebrate Pathology*, 30, 442-443 (1977)]. Therefore it is possible to check, e.g., from the amino acid sequence of the polyhedrin protein, to which portion of the polyhedron gene a BmNPV-derived DNA fragment corresponds on whether the fragment is from some other portion than the gene by determining the base sequence of the fragment, constructing an amino acid sequence based on the base sequence according to the codon-amino acid correspondence rule and comparing the amino acid sequence so obtained with that reported by Serebraini et al., supra.

The present inventors have ascertained that, to eliminate the polyhedrin gene and to utilize the upstream and downstream DNA fragments, a BmNPV DNA fragment (about 10.6 kbp) obtainable by EcoRI cleavage is best suited and that cleavage of the fragment with HindIII (produced by Takara Shuzo Co., Ltd.) gives two fragments which are convenient to use. However, the fragment is not the only one with which the objects of the invention can be achieved. Other appropriate fragments, e.g., cleavage-582, obtained by screening using various restriction enzymes could be used.

In the description which follows, the case where the above-mentioned suitable fragment will be used is described for the purposes of illustration where appropriate. The DNA sequences and so on will be indicated, unless otherwise specified, in a conventional manner. Thus, the 5' end is given on the left side and the 3' end on the right side, and a fragment resulting from restriction enzyme cleavage is indicated by a hyphen between the names of the restriction enzymes. In this case, too, the left and right have the same meanings as mentioned above.

For example, the EcoRI-EcoRI fragment mentioned above is summarized below.

Figure 1:
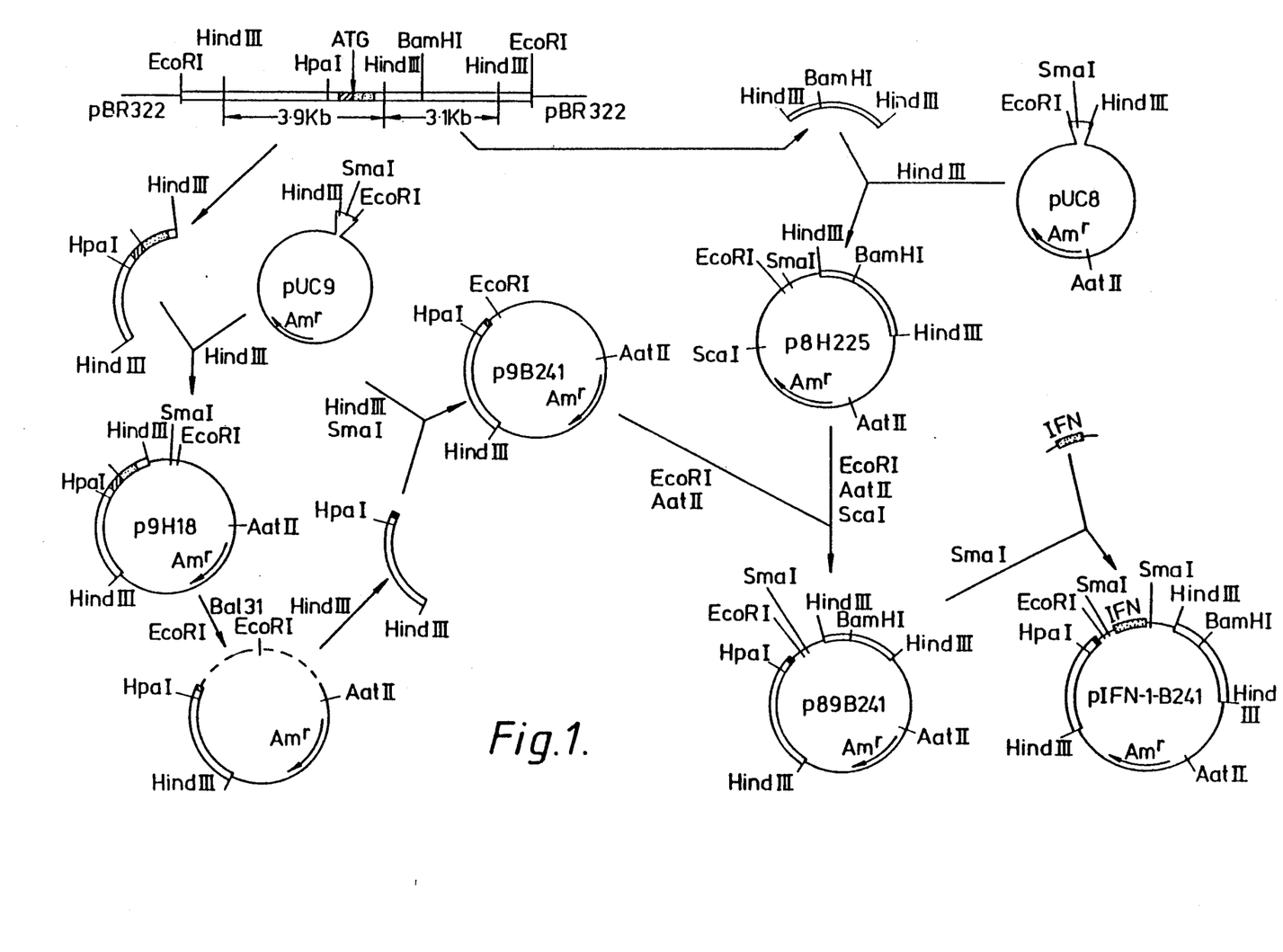
FIG. 1 outlines the construction of a pIFN-1B series plasmid which is useful to produce recombinant BmNPV DNA.
Figure 2:
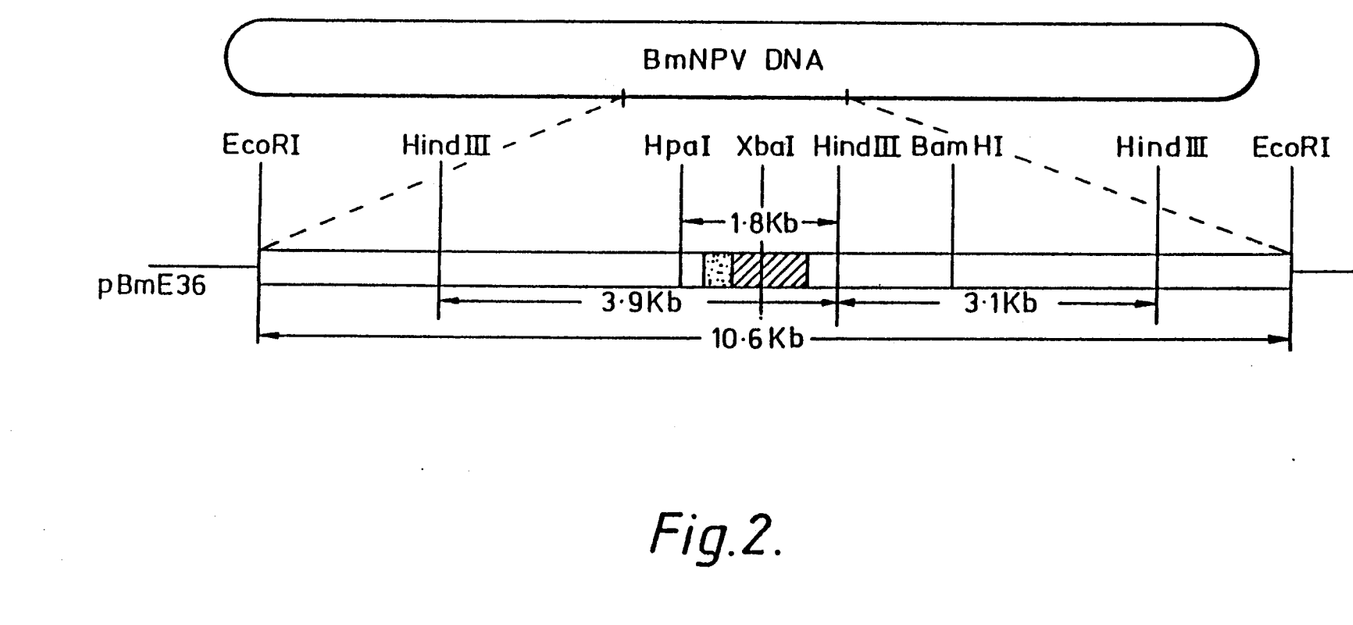
FIG. 2 shows a restriction enzyme map of the EcoRI-EcoRI fragment of pBmE36.
Figure 3A:
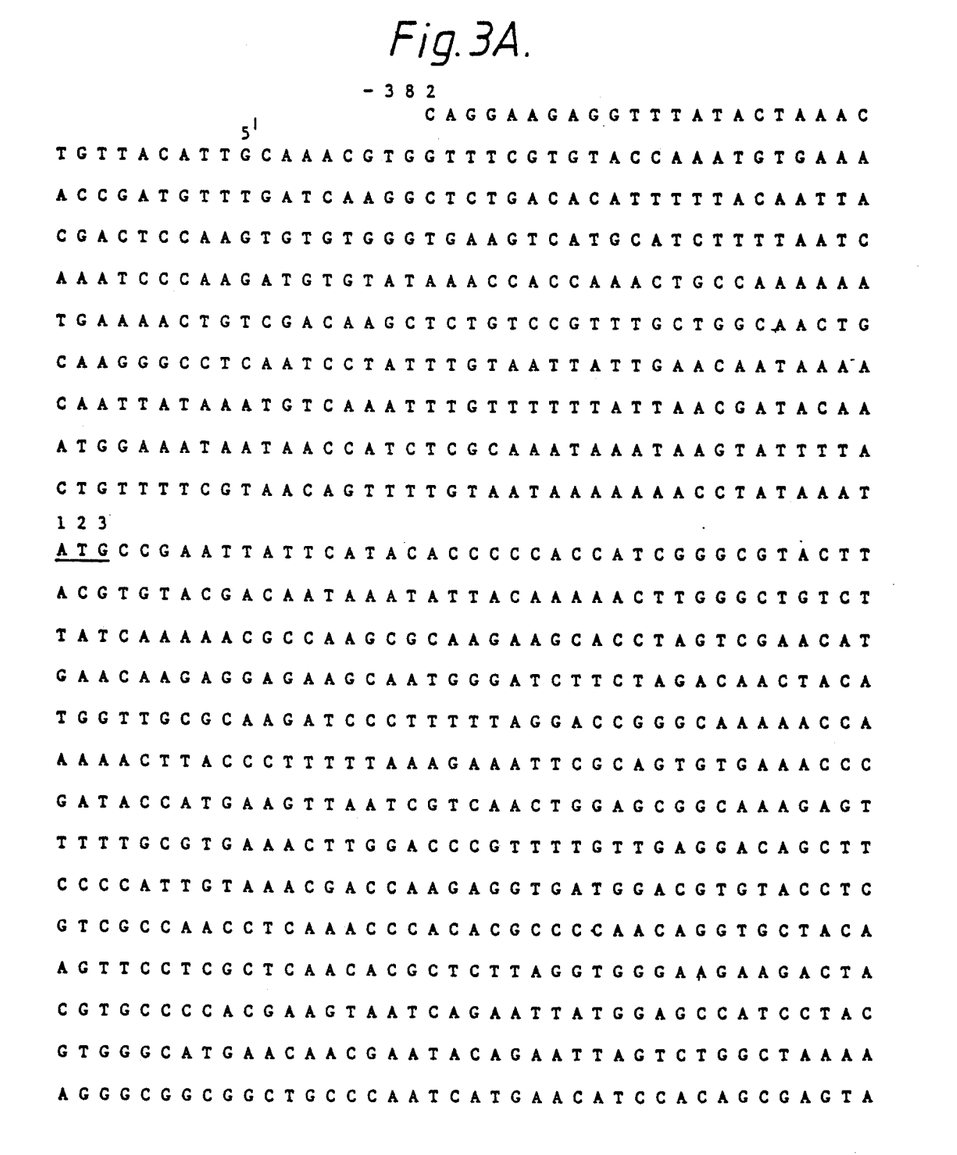
FIG. 3 is the base sequence of a part of the HpaI-HindIII fragment.
Figure 3B:
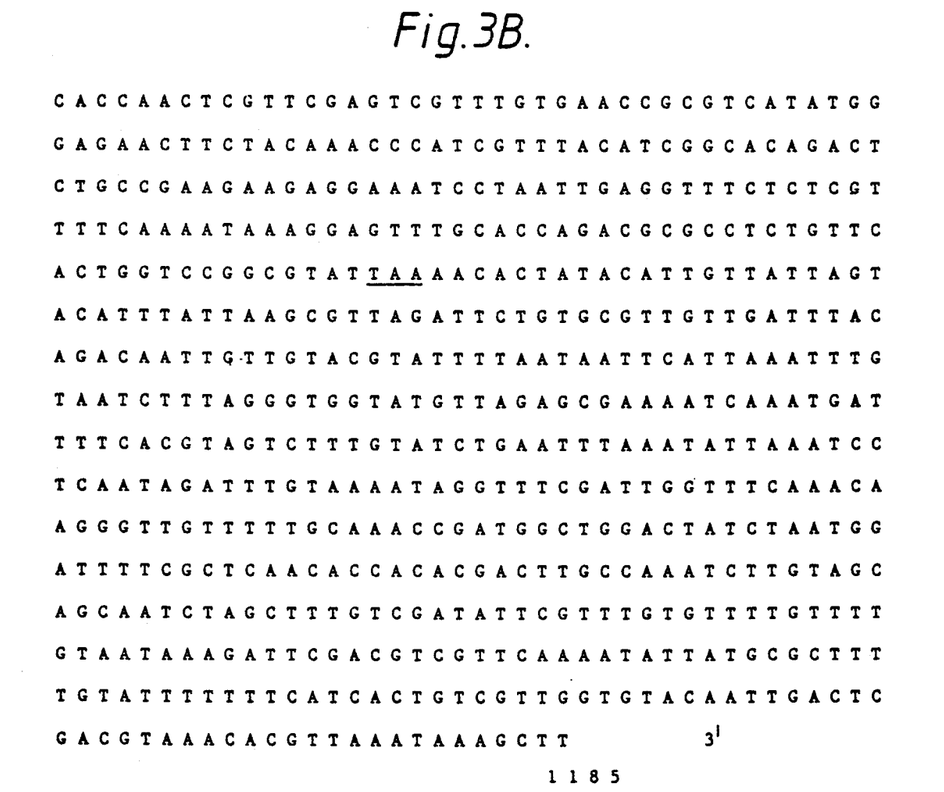

The gene portion coding for polyhedral protein can be detected by further cleavage of the above fragment into smaller fragments followed by screening thereof by Southern hybridization, for instance. Thus, in the above case, the presence of the structural gene in question could be confirmed in an HpaI-HindIII fragment (about 1.8 kb). HpaI is produced by Takara Shuzo Co., Ltd. For reference, the base sequence of a part of the HpaI-HindIII fragment [from the base at 201 downstream from the HpaI cleavage site to the HindIII cleavage site (1567 bp from −382 to 1185 with reference to the ATG start site is given in FIG. 3. For the utilization of the portions upstream and downstream from the structural gene, it is therefore convenient to use two fragments, HindIII-HindIII (about 3.9 kb) and HindIII-HindIII (about 3.1 kb) fragments prepared by HindIII treatment. These two fragments can be isolated by conventional methods such as agarose electrophoresis as described in Mol. Clon., pp 164-167.

The two fragments thus isolated are conveniently manipulated by inserting them separately into plasmids containing artificial linkers. Commercially available plasmids pUC9 and pUC8 (both from Pharmacia P-L Biochemicals), for instance, are suited for that purpose.

The HindIII-HindIII fragment (about 3.1 kb) from the downstream side is utilized by inserting the same into pUC8 at the HindIII site thereof. The upstream-side HindIII-HindIII fragment which contains the gene for polyhedral protein is inserted into pUC9 at the HindIII site thereof, the insertion product is cleaved at one site with a restriction enzyme (e.g., EcoRI), and the DNA fragment thus obtained is subjected to Bal31 (produced by Bethesda Research Laboratories, USA) digestion, whereby the DNA chain length can be conveniently adjusted since Bal31 digests the bases one by one from both cleavage site ends. By producing several fragments differing in length by varying the treatment time and analyzing them for base sequence, it is possible to determine the fragment now free of the polyhedrin gene from knowledge of the base pairs in the polyhedrin gene DNA sequence.

After eliminating the polyhedrin gene in the above manner, a DNA fragment containing the virus-derived promoter region upstream from the gene can be obtained. This fragment is useful in producing a vector plasmid by inserting this fragment, in combination with a DNA fragment downstream from the polyhedrin gene, which is also obtainable in the above polyhedrin gene elimination, in this sequence into a plasmid and further in producing a recombinant plasmid by then inserting an exogenous gene for a useful substance into the site between both of the fragments which is the former site where the polyhedrin gene was present.

For instance, the upstream portion, after treatment with HindIII, is inserted into pUC9 to produce a plasmid, whereas the downstream portion is inserted in the form of a HindIII-HindIII fragment (about 3.1 kb) into pUC8 at the HindIII site to produce another plasmid. Then, taking advantage of restriction enzyme sites common to both of the plasmids, a further plasmid is constructed which contains both the upstream and downstream portions as if they had been inserted into one and the same plasmid. In this case, it is sometimes convenient in inserting a gene for a useful substance to design such that an artificial linker portion occurs between both of the portions. Other conventional methods of DNA sequence insertion into a plasmid can be used also.

Where deletions are found in and around the translational start codon for the polyhedrin gene and in and around the translational termination codon, by comparison with the DNA sequence given hereinafter they may be filled by supplementary addition of synthetic DNAs or by in vitro mutagenesis as described in K. Itakura et al., Nucleic Acid Res., 9, pp 3647-3156, (1981). Such repairs are made using conventional recombinant DNA techniques as described in Mol. Clon.

For the production of useful substances, there have been reported a variety of genes and, besides, it is expected that isolation of many natural genes and synthesis of such and other genes will be reported in the future. It will be easily understood that all of them can be used in the practice of the present invention. Useful substances include biologically active material, e.g., peptides, proteins and glycoproteins, e.g., lymphokines such as α-interferon, β-interferon, γ-interferon, TNF and interleukins, hormones such as insulin and human growth hormone, vaccines such as human hepatitis A and B, and influenza vaccines, and other materials such as TPA, somatomedins, colony stimulating factors. In general the translational start codon ATG can be joined to these genes for useful substance production prior to subsequent procedural steps.

A recombinant plasmid is then produced by inserting a gene for the production of a useful substance, with a polylinker, which contains restriction sites of EcoRI, SmaI, BamHI. SalI and PstI, joined to both ends thereof, into the vector or by some other appropriate conventional method as described in *Mol. Clon.*, pp 392–393. Consequently, the thus-obtained recombinant plasmid contains the virus-derived fragments, namely the promoter region-containing DNA fragment and the downstream DNA fragment starting from the translational termination codon, upstream and downstream from the exogenous gene for useful substance production, respectively, as well as the exogenous gene. In the procedural steps mentioned above, a reversal of the base sequence may possibly take place during DNA fragment inserting. Therefore it is of course necessary to confirm in each step, prior to proceeding to the next step, that the base sequence has the correct reading directionality.

The recombinant plasmid obtained in the above manner can itself be used for the transformation of *Escherichia coli* and be propagated therein.

It is not always necessary for the 5'-upstream fragment containing the promoter region to retain the base sequence originally occurring in the BmNPV DNA. Similar expression rate can be expected even when the fragment has been more or less modified.

The typical TATA box said to be present in the promoter region in general cannot be identified in a definite manner in that portion of the BmNPV DNA which is upstream from ATG of the structural gene for polyhedral protein. However, as shown in Example C-2 hereinafter and the succeeding examples as well as in Table 1, some deficiencies in the upstream portion from ATG, namely deletions in $-7$ to $-1$ bp, $-18$ to $-1$ bp and $-19$ to $-1$ bp, have no substantial influence on the excellent effect which is obtainable without such deletions. A satisfactory result can be produced also with a deletion of $-29$ to $-1$ bp. On the other hand, deletion of $-82$ to $-1$ bp results in a tendency toward a considerably reduced effect. Therefore, the vicinity of the $-80$ base from ATG appears to already include an important promoter region. The 5'-upstream DNA, which comprises a combination of the promoter region and an upstream DNA useful for viral DNA recombination, may be variable in length. For instance, it can have a length in the range of several hundred to about 10 kilo base pairs which precede ATG. More specifically, as will be mentioned later herein, the use of that portion of the HpaI-HindIII fragment of about 1.8 kb which is upstream from ATG or the use of that portion of the HindIII-HindIII fragment of about 3.9 kb which is upstream from ATG or of a part thereof gives satisfactory results. Apparently, it is not essential that the 5'-upstream DNA contain a further portion upstream from the fragment of about 3.9 kb. The promoter region is important for excellent protein productivity of BmNPV DNA to be exploited, as already mentioned hereinabove.

The DNA sequence located upstream from the promoter region and the 3'-downstream DNA sequence downstream from the structural gene for polyhedral protein are important as keys for the production of a recombinant virus by insertion of a gene coding for a useful substance (with the translation start codon for the exogenous gene coding for useful substance) into the BmNPV DNA as described later. Thus, mixed infection with the BmNPV DNA and a recombination DNA for transfer (e.g., plasmid) which has a DNA fragment containing a gene coding for a useful substance and, upstream and downstream from this gene, DNA sequences homologous to the respective counterparts in the BmNPV DNA results in crossover and transfer of the gene coding for the useful substance to the BmNPV DNA due to the homology in the key portions to provide a recombinant BmNPV DNA.

The determination, modification and utilization of the respective DNA sequences in the portions upstream and downstream from the structural gene for polyhedral protein are by no means difficult for one skilled in the art to perform when the description given herinabove and hereinbelow as well as in the examples are referred to. One skilled in the art can understand and practice the relevant techniques, however detailed they might be, with only routine experimentation. It is to be noted that any mode of embodiment which is practicable in that manner falls within the scope of the present invention.

By using the above-mentioned recombinant plasmid, various methods can be used to produce a recombinant BmNPV DNA containing the gene coding for a useful substance. For instance, one method is conducted in vitro and another uses the silkworm. In a further embodiment, such a recombinant plasmid is not used but a recombinant is produced between the BmNPV DNA and pBR322 or the like and the polyhedrin gene in the recombinant is replaced by a gene coding for the production of a useful substance to produce a recombinant viral DNA.

In vitro mixed infection of cultured cells, for example, cells of an established cell line (Bm cells which are described as BM-N cell in L. E. Volkman and P. A. Goldsmith, *Appl. Environ. Microbiol.*, 227–233 (1982) or Bm cells deposited at ATCC under accession number CRL-8851) from *Bombyx mori* or other cells susceptible to infection by BmNPV which can be determined by visual examination, cytopathic effects, etc., with the BmNPV DNA and a recombinant plasmid having a gene coding for the production of a useful substance results in crossover and transfer of the desirable gene (gene coding for useful substance production) to the viral DNA to produce a recombinant viral DNA (recombinant BmNPV DNA). This recombination is achieved in some instances in the manner of substitution of the desirable gene for the polyhedral protein structural gene region and, in other instances, in the manner of additional insertion of one or a plurality of genes for useful substance production into the viral DNA in some other region or regions therein. Such mixed infection effected in vitro results in propagation of the recombinant viral DNA and, consequently, in accumulation of the desired useful substance. The medium may contain the nonrecombinant as well as the recombinant virus but the recombinant virus can be isolated by a conventional method, for example by the dilution method or plaque method as described in H. A. Wood, *J. Invertebr. Pathol.*, 29, 304–307 (1977) and S. Maeda, *J. Seric. Sci. Jpn.*, 53, 547–548 (1984).

The above mixed infection may also be effected in the silkworm.

By infecting Bm cells in vitro with the virus grown in Bm cells (either a mixture of the recombinant and non-recombinant viruses or the recombinant isolated therefrom) or injecting the virus percutaneously into the silkworm or into the body cavity thereof, the desired useful substance can be produced efficiently. Further, the silkworm can be infected with the virus through the mouth. The useful substance can then be isolated and purified by appropriate known methods, e.g., affinity column chromatography, ion exchange chromatography, molecular sieving, etc.

In accordance with the invention, it is thus possible to produce useful peptides, proteins and glycoproteins safely and economically in large quantities.

In accordance with the invention, a peptide or protein is produced in eukaryotic cells. Therefore, when a gene derived from a eukaryote is used, the peptide or protein produced can undergo the same modifications as those which occur in vivo in the eukaryote, such as signal peptide elimination and sugar chain addition, so that the utility of the products is expected to be much higher as compared with the products obtainable by the conventional genetic engineering techniques using bacteria. Moreover, these products can be purified very easily since they are secreted from the cells, e.g., by affinity chromatography, ion exchange chromatography, molecular sieving, etc.

Furthermore, mankind has years of experience in silkworm raising and a huge accumulation of research results, so that large scale silkworm culture is easy to perform. Today it is also possible to raise the silkworm on artificial feed (e.g., "Vita-Silk", a product of Vita-Silk Co., Ltd., Nagoya, Japan). Therefore, the production of useful substances at the living organism level using viral vectors is presumably by far more suited for industrial purposes and more economical than the production of such substances at the cell level.

The following examples in which the production of α-interferon (α-INF), a protein useful as a drug, using the α-INF gene as the gene for useful substance production is described will illustrate a mode of practice of the present invention in further detail. It is to be noted, however, that the examples are by no means intended to limit the scope of the present invention.

EXAMPLE 1

A. Cloning and Propagation of BmNPV by Plaque Technique

Silkworms *Bombyx mori* at the third instar were orally infected with BmNPV. Several days later, the body fluid was collected, diluted with TC-10 medium [*J. Invertebrate Pathology*, 25, 363-370 (1975)] containing 1% fetal calf serum and used for infection of Bm cells [an established cell line of *Bombyx mori* (which was supplied by Dr. L. E. Volkman, University of California, Berkeley, ATCC No. CRL-8910), *Appl. Environ. Microbiol.*, 44, 227-233 (1982)] cultured in the form of monolayer. The infected cells were layered onto TC-10 medium containing 0.75% agarose and 5% fetal calf serum. After medium solidification, incubation was conducted at 27° C. for several days. The plaques formed on the plate were isolated using a Pasteur pipette. Two repetitions of this plaque technique procedure gave genetically homogeneous viral isolates. The strain BmNPV T3 typical of these viral isolates, was used in the subsequent experiment.

The strain T3 was propagated in Bm cells and then used for percutaneous inoculation for infection of silkworms at the fifth instar. Six days later, the infected tissue containing polyhedra formed, with distilled water added thereto, was centrifuged, and the sediment was suspended in distilled water and triturated. The polyhedra were purified by fractional centrifugation (3,000 rpm, 30 minutes) and discontinuous density-gradient centrifugation (45% and 55% (w/w) sucrose solutions, 20,000 rpm, 30 minutes). The polyhedrin suspension was subjected to fractional centrifugation for sucrose solution removal (3,000 rpm, 10 minutes), the purified polyhedra were suspended in 0.1M sodium carbonate (pH 11)-0.05M sodium chloride and treated at 25° C. for 30 minutes to thereby cause release of viral particles. This viral suspension was subjected to 10 to 40% (w/w) sucrose density gradient centrifugation (18,000 rpm, 30 minutes) for purification. The sucrose was removed by dialysis or fractional centrifugation (40,000 rpm, 30 minutes) to give purified viral particles.

B. Preparation of Viral DNA, Identification of Polyhedrin Gene, and Cloning

B-1 Extraction of Viral DNA

To the thus-obtained virus-containing solution, there were added SDS (sodium lauryl sulfate, 1 w/w %) and protease K (Merck, 1 mg/ml). After about 2 hours of incubation at 37° C., an equal volume of a phenol solution [saturated in 10 mM Tris-hydrochloride buffer (pH 7.6)-1 mM EDTA] was added to the above solution, and the mixture was gently shaken for about 5 minutes and then centrifuged at 12,000 rpm for 5 minutes. The aqueous layer was taken, and the same phenol treatment was repeated twice. To this DNA-containing aqueous layer was added an equal volume of chloroform, followed by gentle shaking for about 5 minutes and centrifugation at 12,000 rpm for 2 minutes. The aqueous layer was taken, the same chloroform treatment was repeated twice, and the aqueous layer was dialyzed against 10 mM Tris-hydrochloride buffer (pH 7.6)-1 mM EDTA for about 2 days. The viral DNA thus obtained (ATCC No. 40188) was used in the subsequent gene cloning and Bm cell transfection.

B-2 Cloning of Polyhedron Gene

Probe Preparation

Silkworms at the fifth instar were percutaneously infected with the strain BmNPV T3. Several days later, whole RNA was extracted from the fat body tissue by the guanidine hydrochloride method and purified using an oligo(dT) cellulose column to give a poly(A)-containing mRNA. This mRNA was examined using the in vitro rabbit reticulocyte (Weissbach, H. and Ochoa, S.; *Ann. Rev. Biochem.*, 45, p 191, 1976) translation system and it was found that the polyhedrin-encoding mRNA accounted for 90% or more of the whole mRNA. A cDNA was synthesized using the mRNA at template, oligo(dT) as primer, and reverse transcriptase as described in *Mol. Clon.*, pp 211-246. On that occasion, $^{32}$P-containing dCTP was used as substrate, and the thus-labeled cDNA was used as a probe for screening for the polyhedrin gene.

Cloning of Polyhedrin Gene-Containing EcoRI Fragment

The purified DNA of BmNPV T3 was digested with EcoRI. The fragments were electrophoresed on 0.7% agarose gel and transferred onto a nitrocellulose filter, followed by hybridization with the above-mentioned probe. A DNA fragment of about 10.6 kb specifically hybridized was inserted into pBR322 at the EcoRI cleavage site thereof. Thus, the viral DNA was digested with EcoRI, followed by the same phenol treatment and chloroform treatment as described above in Paragraph B-1 above. The aqueous layer was separated, a 1/20 volume of 4M sodium chloride and 2 volumes of cold ethanol were added thereto, and the precipitate DNA was dissolved in a small amount of Tris buffer [10 mM Tris-hydrochloride (pH 7.6)-1 mM EDTA]. Separately, pBR322 was digested with EcoRI, then treated in the same manner as above, further treated with BAP [bacterial alkaline phosphatase (Bethesda Research Laboratories)], again subjected to phenol treatment and chloroform treatment as described hereinbefore, and precipitated by addition of ethanol. The precipitate was dissolved in a small amount of Tris buffer.

These EcoRI digestion products from the viral DNA and pBR322 were subjected to ligation at 5° C. for 10 hours with T4 ligase added. The ligation product was introduced into commercially available *Escherichia coli* K12 JM83 and the resultant tetracycline-resistant transformants were screened by colony hybridization using the above-mentioned labeled cDNA as a probe. Thus, an *Escherichia coli* strain carrying a plasmid containing an EcoRI fragment of about 10.6 kb with the polyhedrin gene contained therein was obtained. This strain was cultivated, and the plasmid DNA was purified by the cesium chloride method and named pBmE36. A strain containing the plasmid pBmE36 was named *Escherichia coli* K12 JM83 DGB-0036 and deposited in Fermentation Research Institute, Agency of Industrial Science and Technology, Japan as FERM BP-813. The restriction enzyme map of the EcoRI-EcoRI insert portion of pBmE36 is shown in Figure. The insert DNA portion was further examined by the Southern hybridization method using the above-mentioned labeled cDNA as probe. The cDNA hybridized only with an HpaI-HindIII fragment (about 1.8 kb).

C. Elimination of Polyhedrin Structural Gene Portion—Construction of p9B Series Plasmids

C-1 Cloning of Polyhedron Gene-Containing Portion and Portion Downstream Therefrom A HindIII-HindIII fragment (about 3.9 kb) containing the above HpaI-HindIII fragment and a HindIII-HindIII fragment (about 3.1 kb) containing a portion downstream from the polyhedrin gene were inserted into commercial cloning vectors pUC9 and pUC8, respectively, at the HindIII site thereof to produce p9H18 and p8H225, respectively.

C-2 Elimination of Polyhedrin Gene Portion

The plasmid p9H18 was cleaved with EcoRI and then treated with Bal31 to thereby pare off part of either side of the cleavage site. By varying the time of Bal31 treatment, fragments differing in length were produced. These were treated with HindIII and separated by 0.7% agarose gel electrophoresis, followed by extraction, which gave various virus-derived DNA fragments differing in length.

pUC9 was treated with SmaI (produced by Takara Shuzo Co., Ltd.) and HindIII, followed by ligation with the DNA fragments previously obtained (having a blunt end and a HindIII end). *Escherichia coli* K12 JM83 was transformed with the plasmids produced and then grown, the plasmids were recovered, and the base sequence from the 3' side of each virus-derived DNA fragment inserted was determined by the dideoxy method (F. Sanger, *Science*, 214, 1205–1210, (1981)) using a primer (15-base sequencing primer of M13) to thereby identify the viral polyhedrin gene portion. Thus, a base sequence corresponding to the amino acid sequence of polyhedral protein as described in Serebraini et al. supra was found among the base sequences of the virus-derived DNA fragments, and the translational start codon ATG was also identified. Among various plasmids obtained depending on the length of Bal31 treatment, the one lacking in the 29 base pairs upstream from the translational start codon ATG for the polyhedrin gene and in the structural gene for polyhedral protein (inclusive of ATG) was named p9B241.

Figure 4:
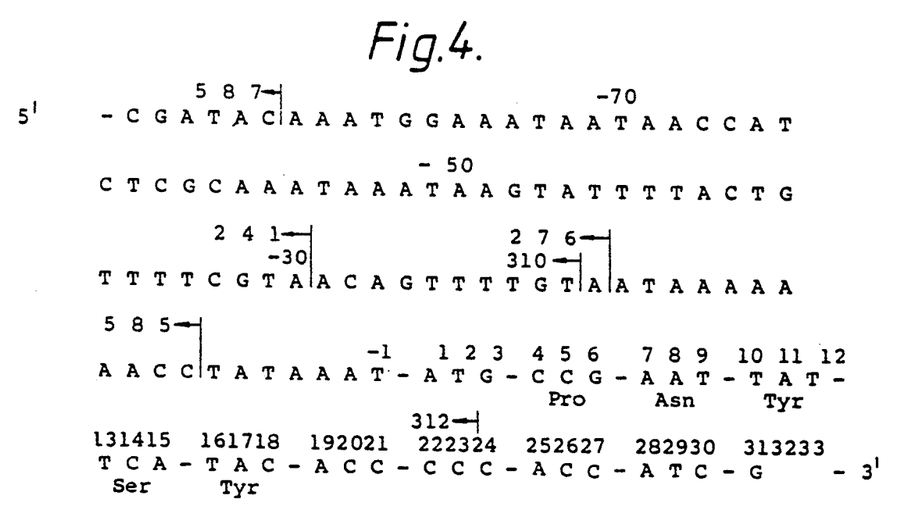
FIG. 4 is the base sequence in the vicinity of the ATG of the polyhedral gene.

Similarly, p9B series plasmids were produced. That is, the ones lacking in the 82 base pairs, 19 base pairs, 18 base pairs and 7 base pairs upstream from ATG and in ATG and the following were named p9B587, p9B310, p9B276. and p9B585, respectively, and the one lacking in the 23 bp downstream from ATG was named p9B312. The base sequence of the region concerned is shown in FIG. 4.

D. Construction of Plasmids Lacking in Polyhedrin Structural Gene Portion

The plasmid p9B241 was treated with EcoRI and AatII (produced by Toyobo Co., Ltd.). Separately, p8H225 [constructed in C-1 above] was treated with EcoRI, AatII and ScaI (produced by New England Biolabs, USA) (an unnecessary pUC8-derived fragment was converted into a small piece with ScaI). Both reaction mixtures were each treated with phenol and then with chloroform and further treated with ethanol for precipitation. The two precipitate DNAs were ligated together, and *Escherichia coli* K12 JM83 was transformed with the resultant plasmids. Plasmids were extracted from the transformants, and a plasmid in which both the virus-derived upstream and downstream DNA fragments were correct in direction was selected. Cleavage with various restriction enzymes showed that this recombinant plasmid had an ampicillin resistance marker and contained an upstream portion of the viral DNA which started from the 30th base pair upstream from the start codon ATG for the polyhedrin gene and extended to a length of about 3 kb upstream from said 30th base pair (this portion including promoter region) and a downstream portion of about 3.1 kb downstream from the termination codon for this gene (but lacking about 300 base pairs downstream from the termination codon) each in the same direction as in the original virus. This was capable of propagating in *Escherichia coli* systems, and was named p89B241. Similarly, p89B587, p89B310, p89B276 and p89B585 were constructed using p9B587, p9B310, p9B276 and p9B585, respectively.

E. Insertion of α-IFN Gene—Construction of pIFN-1-B241

(i) The luekocyte IFN gene was searched for from among a human genome λ phage Charon 4A recombinant library [Lawn et al., *Cell*, 15, 1157–1174 (1978)], and the thus-obtained DNA containing the α-IFN-J gene was treated with HindIII and EcoRI, and an α-IFN-J gene-containing fragment was isolated by agarose gel electrophoresis and ligated with HindIII- and EcoRI-treated pUC9. *Escherichia coli* K12 JM83 was transformed with the plasmid obtained. The plasmid was recovered from the transformant and treated with MstII (produced by New England Biolabs, USA) and PvuII (produced by Takara Shuzo Co., Ltd.), an α-IFN-J gene-containing DNA fragment was isolated and a SmaI linker (produced by Takara Shuzo Co., Ltd.) was joined to both ends of the fragment. The joined product was treated with SmaI and ligated with a SmaI fragment from the plasmid p89B241 obtained in D above to give a recombinant plasmid. After confirming that the -IFN-J gene had been inserted in this plasmid in the correct direction, *Escherichia coli* K12 JM83 was transformed with this plasmid and grown, whereby a large quantity of plasmid was produced. This plasmid was named pIFN-1-B241. In this plasmid, a portion upstream from the polyhedrin gene (from about −3 kb base pair to −30 base pair) was followed by a 13 bp residue of the linker used in the construction of the plasmid p89B241 and further by a 32-bp 5′-nontranslational region of the chromosome-derived α-IFN-J gene, which region was in turn followed by the α-IFN-J gene beginning with ATG and having the correct direction. Further there was a portion downstram from the polyhedrin gene (from a base pair about 300 bp downstream from the termination codon to a base pair about 3.1 kbp downstream from this base pair) connected to the α-IFN-J gene.

(ii) Insertion of α-IFN Gene—Construction of pIFN-2B Plasmids

*Escherichia coli* K12 JM83 was transformed with the above plasmid, namely the product of ligation of the above-mentioned α-IFN-J gene-containing HindIII-EcoRI fragment with pUC9. The plasmid was recovered from the transformant and treated with HpaII (produced by Takara Shuzo Co., Ltd.), and an α-IFN-J gene-containing DNA fragment was separated and ligated with the product of annealing of a chemically synthesized oligomer (CGGGCCATC) phosphorylated using $^{32}$P-ATP and T$_4$ polynucleotide kinase (produced by Takara Shuzo Co., Ltd.) with another synthetic oligomer (CCGGGATGGCC). The ligation product was separated by agarose gel electrophoresis followed by extraction, then again phosphorylated using $^{32}$P-ATP and T$_4$ polynucleotide kinase and ligated with an XmaI (produced by New England Biolabs, USA) fragment of the plasmid p89B241 obtained in D above to give a recombinant plasmid. After confirmation of the fact that the α-IFN-J gene had been inserted in this plasmid in the right direction, *Escherichia coli* K12 JM83 was transformed with the plasmid and grown, whereby the plasmid was produced in a large quantity. This plasmid was named pIFN-2-B-241.

In this plasmid, an upstream (from the polyhedrin gene) portion (from a base pair about 3 kb upstream to −30 base pair) was followed by a 13-bp residue of the linker used in constructing the plasmid p89B241, then by the α-IFN-J gene beginning with ATG and inserted in the correct direction and further by a downstream (from the polyhedrin gene) portion (from a base pair about 300 bp downstream from the termination codon to a base pair about 3.1 kb downstream from said base pair).

pIFN-2-B587, pIFN-2-B310, pIFN-2-B276 and pIFN-2-B585 were constructed in the same manner using p89B587, p89B310, p89B276 and p89B585, respectively, as starting materials.

(iii) Synthesis of Linker

Figure 5:
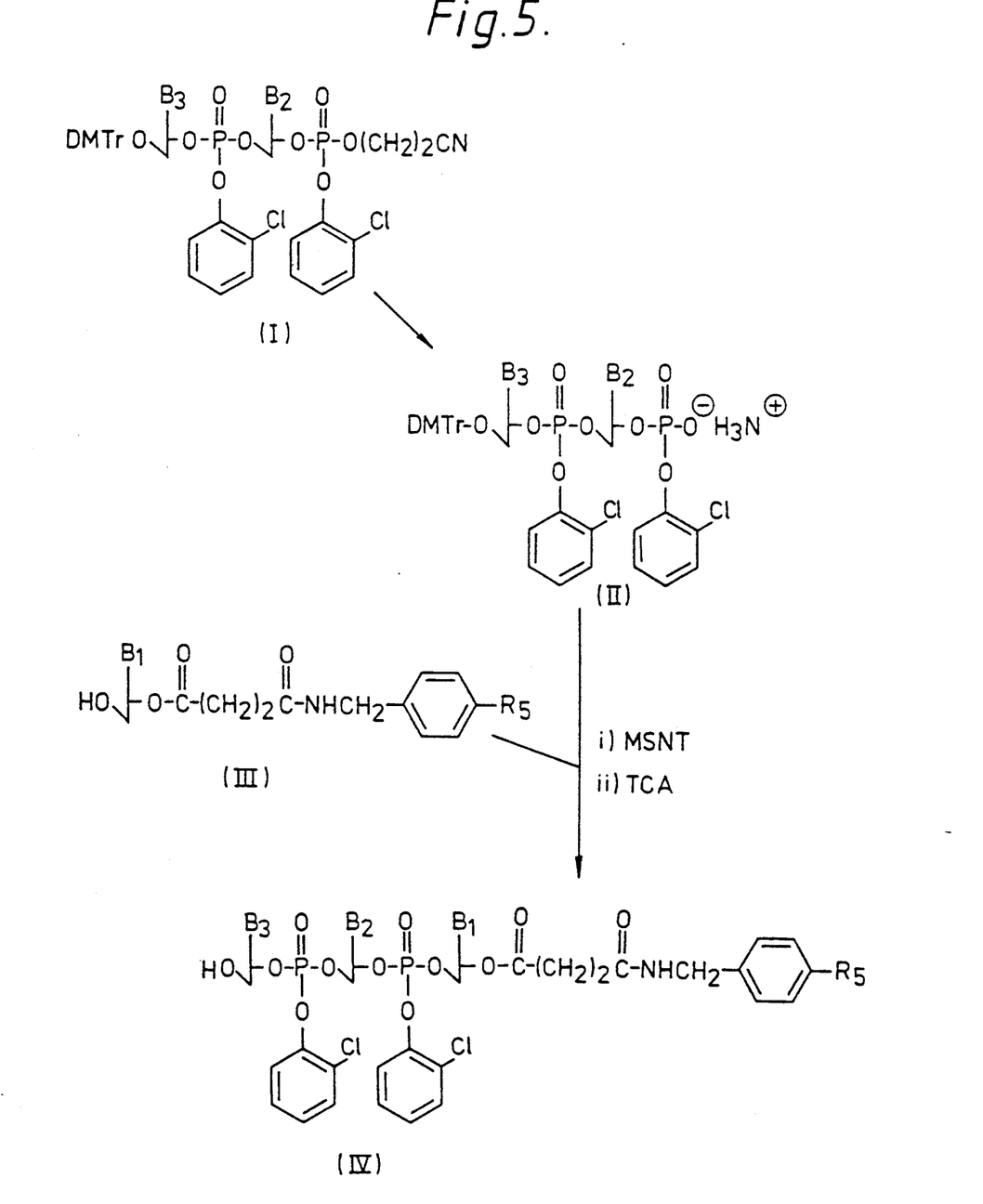
FIG. 5 shows an outline of linker synthesis.

Chemical Synthesis of Oligodeoxyribonucleotides: According to the method described in H. Ito et al. [*Nucleic Acids Research*, 10, 1755 (1982)] and as shown schematically in FIG. 5, oligomers were synthesized by the solid phase method using a polystyrene resin. Thus, a completely protected difunctional dimer (I) (about 100 mg) was converted to the corresponding 3′-phosphodiester (II) by treatment in a tert-butylamine-pyridine (1:9 v/v) solution and the 3′-phosphodiester (II) was condensed with a 5′-free nucleoside resin (III) using the condensing agent mesitylenesulfonylnitrotriazolide (MSNT, 100 mg). The 5′-hydroxyl group of the untreated resin (III) was acetylated using an acetic anhydride-pyridine (1:9 v/v) solution. The subsequent treatment in 2% trichloroacetic acid (TCA)-methylene chloride gave a detritylation product (IV). The above series of reactions was repeated until a specific desired sequence was obtained. To the thus-obtained oligomer-bound resin (about 20 mg) was added 0.5 ml of 0.5M tetramethylguanidine-pyridine-2-aldoxime [in pyridine-water (15:4 by volume)]. After 8 hours of reaction at 37° C., the reaction mixture was treated with concentrated aqueous ammonia at 55° C. for 8 hours. Gel filtration of the solution using a Sephadex G-50 (a cellulosic resin produced by Pharmacia) fine column (2.5×60 cm) gave a DMTr-oligomer. This oligomer was further purified by high performance liquid chromatography (HPLC) using a reversed-phase column (SSC-ODS-272, 0.6×20 cm) and solutions A (0.02M triethylammonium acetate, pH 7.0) and B (50% acetonitrile in 0.02M TEAA, pH 7.0) to produce a linear concentration gradient. The DMTr-oligomer thus purified was treated with 80% acetic acid at room temperature for 20 minutes to thereby effect detritylation, followed by the same HPLC as above. Dialysis of the eluate against 10 mM Tris HCl (pH 7.5)-1 mM EDTA (pH 8.0) gave a desired oligomer. The homogeneity of the completely deprotected oligodeoxyribonucleotide thus obtained was ascertained by the fact that reversed phase column chromatography gave only one single peak and by the fact that 15% polyacrylamide gel-7M urea electrophoresis following labeling of the 5′ end using [γ-$^{32}$P]-ATP and T$_4$ polynucleotide kinase gave only one single band.

(iv) Insertion of α-IFN Gene—Construction of pBM 034

Figure 6:
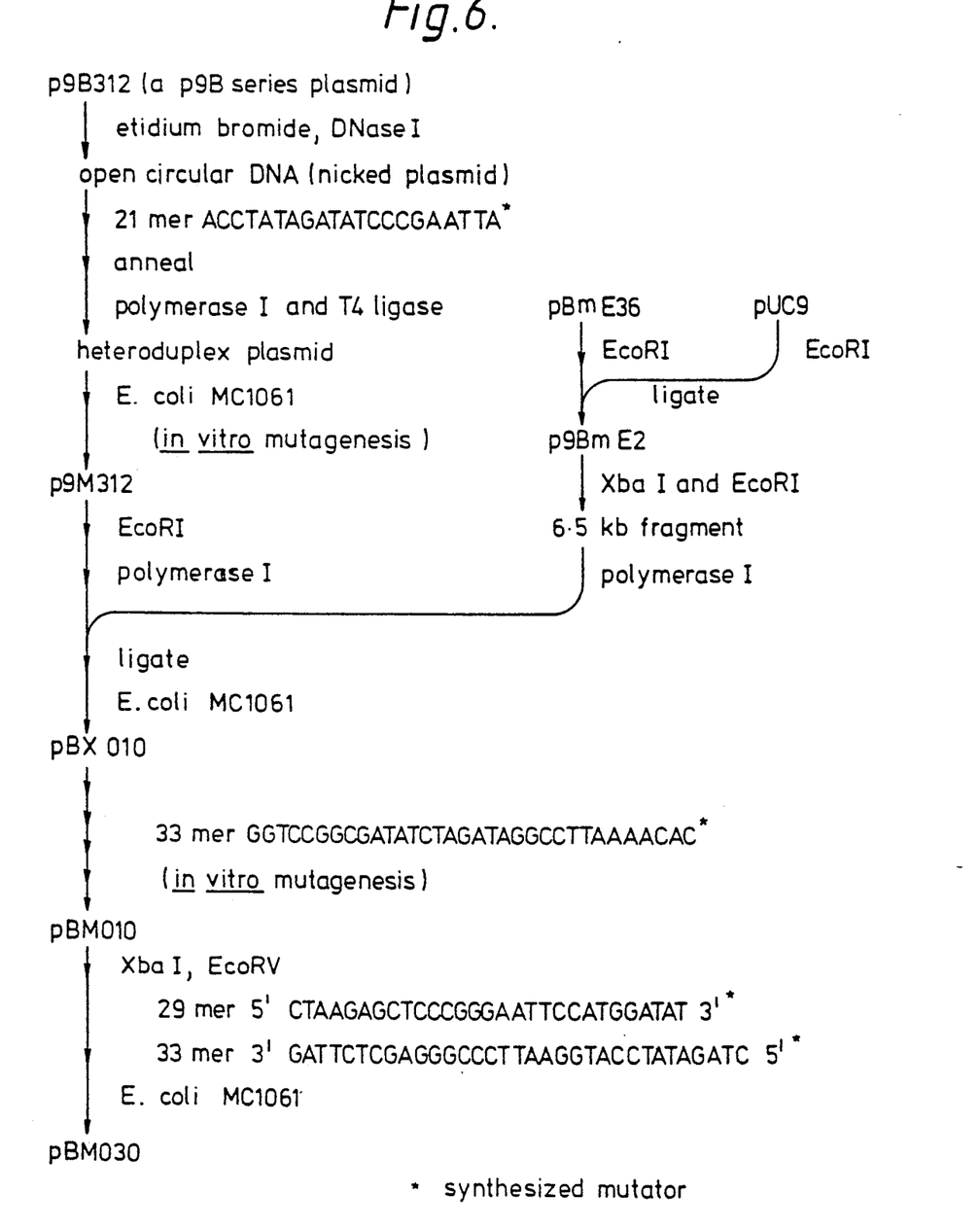
FIG. 6 illustrates a process for preparing pBM030.
Figure 7:
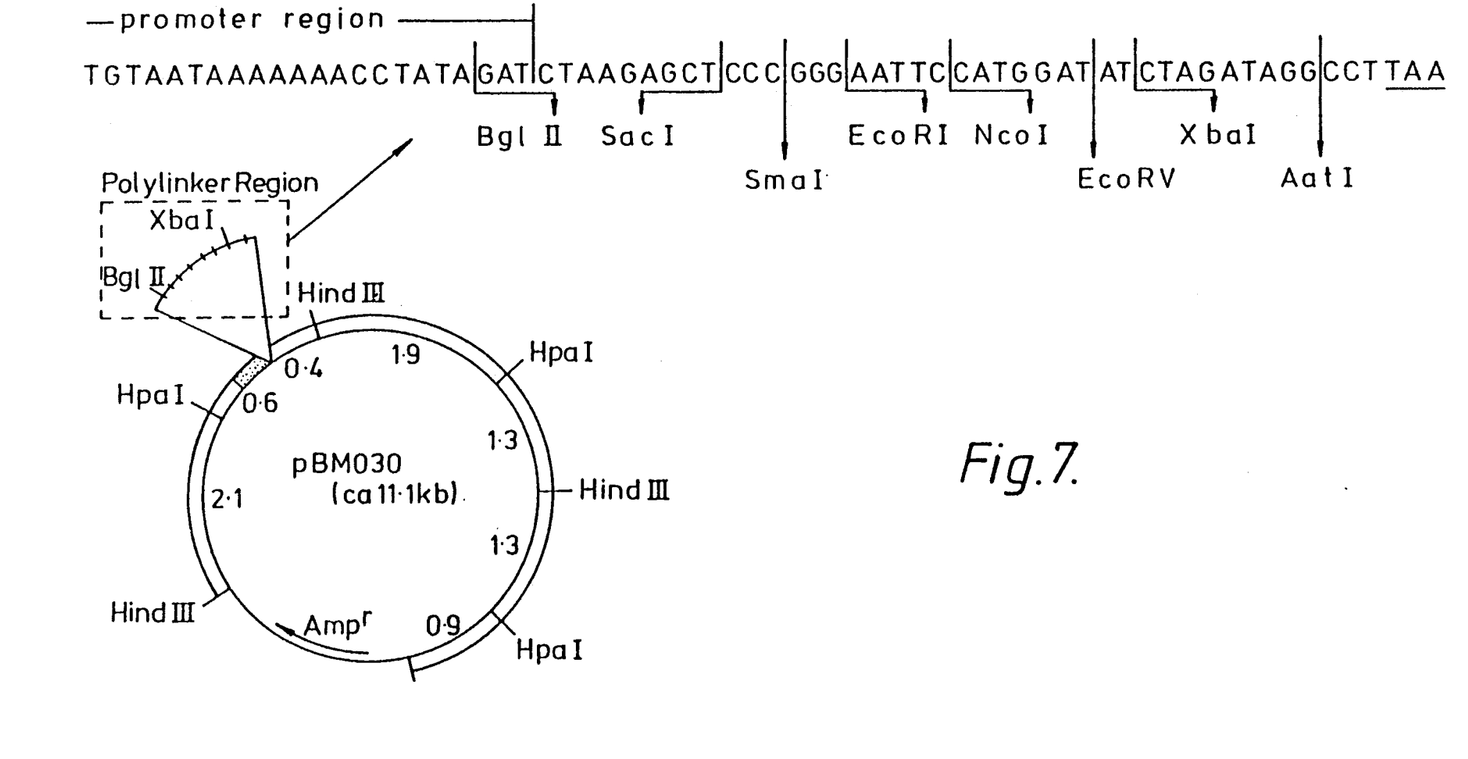
FIG. 7 is a restriction enzyme map of pBM030 showing base sequence of the polylinker region thereof and restriction enzyme cleavage sites therein.
Figure 8:
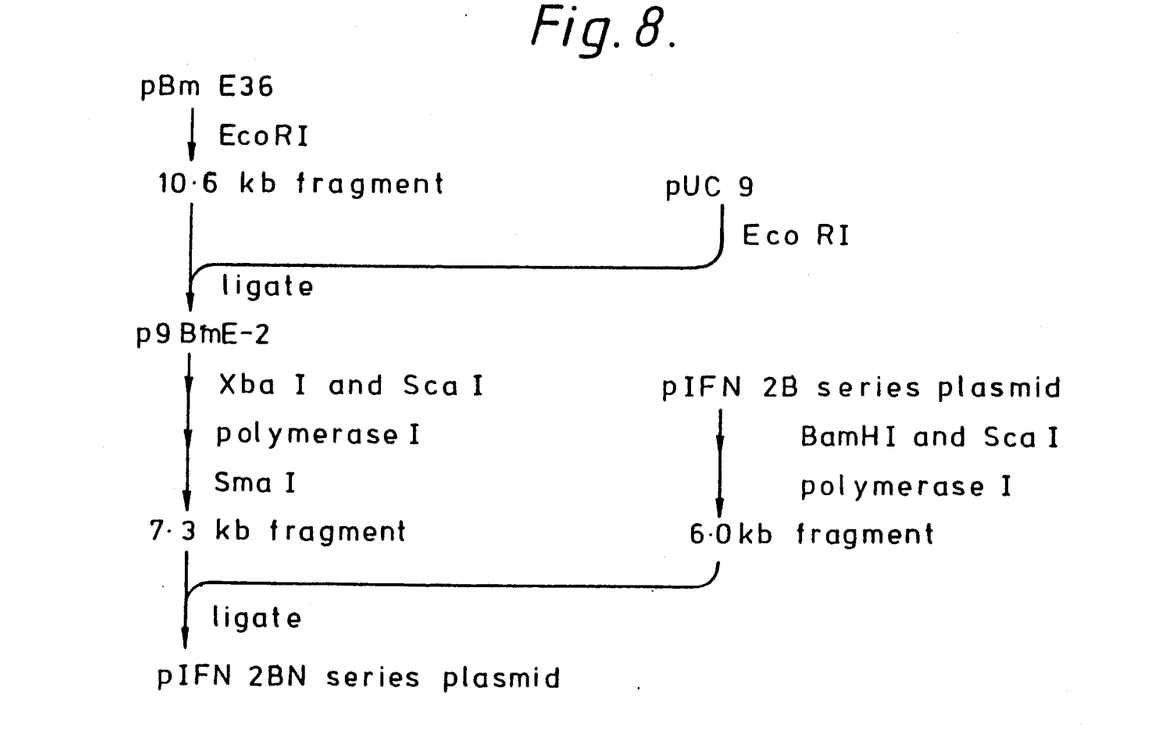
FIG. 8 illustrates a process for preparing pIFN 2 BN series plasmids.

The plasmid pBM 030 was prepared from the plasmid p9B 312 as shown in FIG. 6. This plasmid has the promoter region and terminator region originally occurring in BmNPV except for three base pairs (3 bp) and has a polylinker between these regions instead of the polyhedral gene as shown in FIG. 7. In FIG. 6, the method of preparing p9M312 from p9B312 is known as in vitro mutagenesis (oligonucleotide directed mutagenesis; *Nucleic Acids Research* 9 (15) 3647–3656 (1981)) which was employed in some other part as well.

Figure 9:
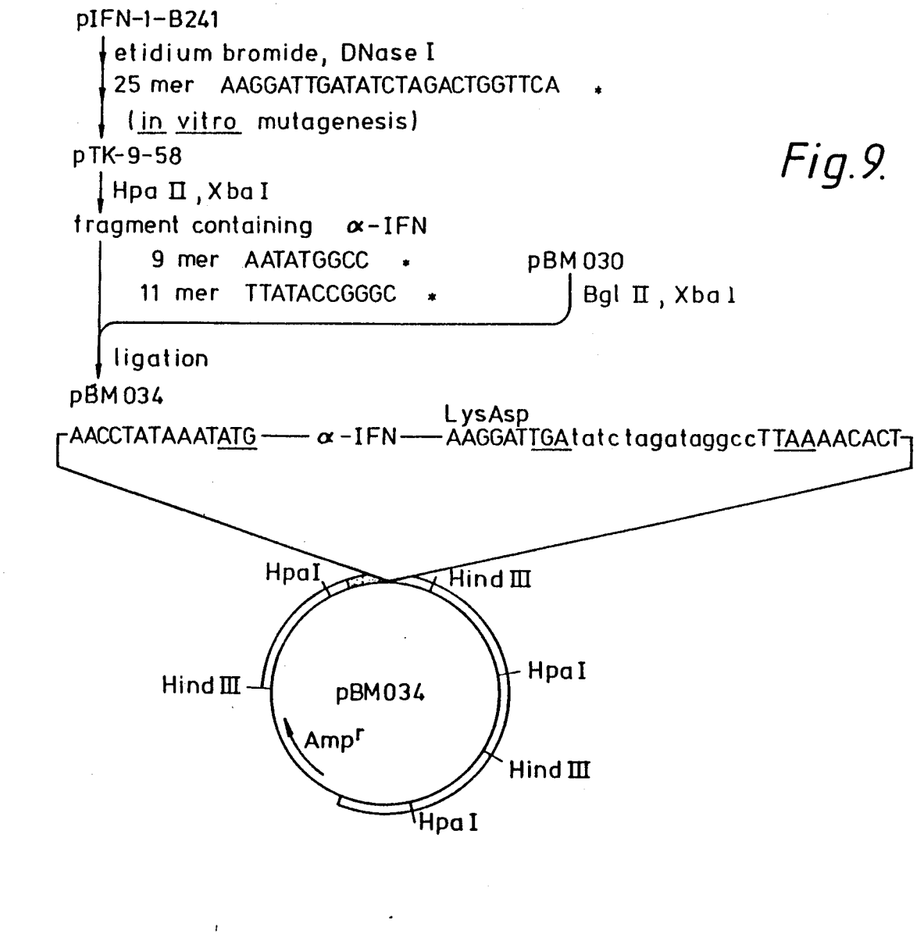
FIG. 9 illustrates a process for preparing pBM034.

To the vector (pBM030), α-IFN gene was inserted by the process shown in FIG. 9 to produce pBM034.

F. Transfection of Bm Cells—Production of Recombinant BmNPV

The BmNPV T3 strain viral DNA (ATCC No. 40188) and pIFN-1-B241, in a proportion of 1:100, were mixed with the solutions I and II having the following compositions, respectively:

| I. | Distilled water | 2.1 ml |
|---|---|---|
| | Carrier DNA (salmon testis, 1 mg/ml) | 50 μl |
| | BmNPV DNA | 10 μl |
| | pIFN-1-B241 DNA | 50 μg |
| | 2 M Calcium chloride | 300 μg |
| II. | 50 mM HEPES buffer (pH 7.1) containing 0.28 M sodium chloride | 2.5 ml |
| | Phosphate buffer (35 mM Na$_2$HPO$_4$-35 mM NaH$_2$PO$_4$) | 50 μl |

A 1-ml portion of the resultant suspension was added to 4 ml of a Bm cell culture medium to thereby introduce the above DNA into cells of *Bombyx mori*. Twenty hours later, the medium was replaced with a fresh portion of medium. After further cultivation for 5 days, the medium was recovered and centrifuged. The clear supernatant was submitted to α-IFN activity assay. Furthermore, the supernatant obtained from the medium recovered by centrifugation at 1,000 rpm for 5 minutes was diluted and subjected to plaque assay. Four days later, plaques were examined under a microscope and polyhedrin-free plaques were selected. Three repetitions of this procedure gave a single viral strain which is a recombinant BmNPV. Bm cells were infected with this viral strain and, after 5 days of cultivation, the medium was recovered.

G. Expression of α-IFN in *Bombyx mori*

Silkworms on day 1 of the 5th instar were percutaneously injected with the medium recovered after 5 days of cultivation as described in F or with the medium recovered after 5 days of cultivation following infection with the single viral strain at a dose of 0.5 ml/head ($10^7$ pfu) and then fed on mulberry leaves at 25° C. for 5 days. Thereafter, a collecting needle was stuck into the abdominal appendage and the body fluid was collected into an ice-cooled Eppendorff tube. The body fluid, with an equal volume of TC-10 medium added, was centrifuged (10,000 rpm, 5 minutes) and the supernatant was assayed for α-IFN activity.

H. Bioassay of α-IFN (i) Activity Measurement

According to the method of C. Philip et al. [*Methods in Enzymology*, 78, 387–394 (1981)], the α-IFN activity assay was performed in the manner of cytopathic effect inhibition (50% CPE inhibition) assay on a 96-well microtiter plate using human amnion-derived FL cells and vesicular stomatitis virus (VSV) while comparing it with an α-IFN standard from the U.S. National Institute of Health (NIH). The results obtained are shown in Table 1 and Table 2 below (for each single viral strain).

TABLE 1

|  | Plasmid | IU/ml |
|---|---|---|
| In cultured Bm cell fluid | pIFN-1-B-241 | $1.2 \times 10^4$ |
|  | pIFN-2-B 241 | $1.3 \times 10^4$ |
|  | pIFN-2-B 587 | 24 |
|  | pIFN-2-B 310 | $1.5 \times 10^4$ |
|  | pIFN-2-B 276 | $1.4 \times 10^4$ |
|  | pIFN-2-B 585 | $4.8 \times 10^4$ |
| In silkworm body fluid | pIFN-1-B 241 | $3.0 \times 10^4$ |

TABLE 2

|  | Plasmid | IU/ml |
|---|---|---|
| In silkworm body fluid | pIFN-2-B-241 | $6.6 \times 10^6$ |
|  | pIFN-2-B 587 | $3.5 \times 10^2$ |
|  | pIFN-2-B 310 | $4.4 \times 10^7$ |
|  | pIFN-2-B 276 | $3.6 \times 10^7$ |
|  | pIFN-2-B 585 | $4.2 \times 10^7$ |
|  | pBM034 | $1.0 \times 10^8$ |

(ii) Determination of N-Terminal of α-IFN

After purification with an antibody column, the N-terminal of α-IFN produced in silkworm using pB034 was determined. The terminal eleven amino acids corresponded to those of the standard α-IFN.

This means that the silkworm cell recognizes correctly the signal sequence of the human protein and expression conducted in the cell with accurate processing.

J. Production of Recombinant BmNPV Containing β-IFN Gene and Expression Thereof In Vitro and In Vivo The phage charon 4A recombinant library of the human genome was screened for β-IFN gene. The thus-obtained DNA containing the β-IFN gene was cleaved by HindII, and β-IFN gene containing fragment was isolated by agarose gel electrophoreses. This fragment was ligated to the HindII site of pUC9. The resulting plasmid was treated with HindII and BglII. The β-IFN gene-containing fragment was isolated by the method described in E. above, and ligated with EcoRV-treated pBM010. This plasmid was named pBM211. Recombinant virus was isolated by the same method described in F. above.

Using thus-obtained recombinant BmNPV, expression was conducted in silkworm by the same method as described in G. above.

When activity of β-IFN was determined using standard sample of β-IFN by the method in H., it was found that the recombinant BmNPV produced about $8 \times 10^5$ U/ml and $8 \times 10^4$ U/ml of β-IFN in the haemolymph and Bm cell, respectively.

The IFN produced by the recombinant virus was neutralized with a monochronal antibody to human β-IFN.

While the invention has been described in detail and with reference to specific embodiments thereof, it will be apparent to one skilled in the art that various changes and modifications can be made therein without departing from the spirit and scope thereof.

What is claimed is:

1. A method for producing a gene product exogenous to *Bombyx mori* nuclear polyhedrosis virus (BmNPV) which comprises the steps of:
   (A) propagating, in living silkworms, a recombinant BmNPV, wherein said recombinant BmNPV comprises the following elements, operably linked in the following order, 5' to 3':
       (i) a 5'-upstream BmNPV DNA fragment originally occurring upstream from the structural gene encoding polyhedral protein and originally having a size sufficient to effect recombination to form said recombinant BmNPV.
       (ii) all or an operable part of the promoter region for said structural gene,
       (iii) a translational start codon,
       (iv) a gene encoding a gene product exogenous to BmNPV and which replaces the entire structural gene encoding polyhedral protein, and
       (v) a 3'-downstream BmNPV DNA fragment originally occurring downstream from said structural gene encoding polyhedral protein and originally having a size sufficient to effect recombination to form said recombinant BmNPV,
   (B) producing said gene product, and
   (C) isolating said gene product.

2. A method for producing a gene product in living silkworms which comprises:
   (A) excising from *Bombyx mori* nuclear polyhedrous virus (BmNPV) DNA a fragment comprising the following elements, operably linked, 5' to 3':

(i) a 5'-upstream BmNPV DNA fragment originally occurring upstream from the structural gene encoding polyhedral protein and originally having a size sufficient to effect recombination with BmNPV DNA to form a recombinant BmNPV, (ii) all or an operable part of the promoter region for said structural gene, (iii) a translational start codon, (iv) a gene encoding the polyhedral protein, and (v) a 3'-downstream fragment originally occurring downstream from said structural gene and originally having a size sufficient to effect recombination with BmNPV DNA to form said recombinant BmNPV;

(B) substituting, in operable linkage, the entire structural gene (iv) with a gene encoding a gene product exogenous to BmNPV to produce a substituted excised DNA fragment, (C) inserting, in operable linkage, the substituted excised DNA fragment into a plasmid capable of recombining with BmNPV DNA to produce said recombinant BmNPV containing said substituted excised DNA fragment, (D) introducing the vector containing the substituted excised DNA fragment and BmNPV DNA into cultured *Bombyx mori* cells for recombination to produce said recombinant BmNPV, (E) propagating the recombinant BmNPV in said living silkworms, (F) producing said gene product, and (G) isolating said gene product.

3. A recombinant *Bombyx mori* nuclear polyhedrosis virus (BmNPV), wherein said recombinant BmNPV comprises the following elements, operably linked in the following order, 5' to 3':

(i) a 5'-upstream BmNPV DNA fragment originally occurring upstream from the structural gene encoding polyhedral protein and originally having a size sufficient to effect recombination to form said recombinant BmNPV.

(ii) a promoter region whose sequence corresponds to the sequence of the promoter region for said structural gene except for the base pair at position $-3$, (iii) a translational start codon, (iv) a gene encoding a gene product exogenous to BmNPV and which replaces the entire structural gene encoding polyhedral protein, and (v) a 3'-downstream BmNPV DNA fragment originally occurring downstream from said structural gene encoding polyhedral protein and originally having a size sufficient to effect recombination to form said recombinant BmNPV.

4. A recombinant DNA vector comprising the following elements, operably linked in the following order, 5' to 3':

(i) a 5'-upstream *Bombyx mori* nuclear polyhedrous virus (BmNPV) DNA fragment originally occurring upstream from the structural gene encoding polyhedral protein and originally having a size sufficient to effect recombination with BmNPV DNA to form a recombinant BmNPV, (ii) a promoter region whose sequence corresponds to the sequence of the promoter region for said structural gene except for the base pair at position $-3$, (iii) a 3'-downstream BmNPV DNA fragment originally occurring downstream from said structural gene and originally having a size sufficient to effect recombination with BmNPV DNA to form said recombinant BmNPV.

5. The recombinant DNA vector as claimed in claim 4, further comprising the following elements, operably linked, 5' to 3', between the promoter region (ii) and the 3'-downstream BmNPV DNA fragment (iii):

(a) a translational start codon, and (b) a gene encoding a gene product exogenous to BmNPV and which replaces the entire structural gene coding for the production of polyhedral protein.

6. Plasmid pBmE36.

7. Plasmid pBM 030.

8. *Escherichia coli* K12 JM83 DGB-0036 having Fermentation Research Institute Deposit No. FERM BP-813.

* * * * *